(12) United States Patent
Di Paolo (10) Patent No.: US 7,576,073 B2
(45) Date of Patent: Aug. 18, 2009

(54) COMBINED THERAPY FOR THE TREATMENT OF PARKINSON'S DISEASE

(75) Inventor: Thérèse Di Paolo, Saint-Agapit (CA)

(73) Assignee: Université Laval (CA)

( * ) Notice: Subject to any disclaimer, the term of this patent is extended or adjusted under 35 U.S.C. 154(b) by 774 days.

(21) Appl. No.: 10/855,493

(22) Filed: May 28, 2004

(65) Prior Publication Data

US 2005/0267085 A1 Dec. 1, 2005

(51) Int. Cl.
*A61K 31/56* (2006.01)
*A61K 31/50* (2006.01)
*A61K 31/135* (2006.01)

(52) U.S. Cl. .................. 514/171; 514/250; 514/649
(58) Field of Classification Search ............... 514/171, 514/250, 649
See application file for complete search history.

(56) References Cited

U.S. PATENT DOCUMENTS

| | | | |
|---|---|---|---|
| 3,838,008 A | | 9/1974 | Bamberg |
| 4,774,244 A | * | 9/1988 | Curtius et al. ............... 514/249 |
| 4,812,447 A | | 3/1989 | Roberts |
| 4,826,875 A | | 5/1989 | Chiesi |
| 5,047,927 A | | 9/1991 | Sowell et al. |
| 5,556,847 A | | 9/1996 | Johnson et al. |
| 5,763,492 A | | 6/1998 | Johnson et al. |
| 6,696,600 B2 | * | 2/2004 | Frenkel et al. ............... 562/445 |
| 2002/0182196 A1 | | 12/2002 | McCleary |

FOREIGN PATENT DOCUMENTS

| | | |
|---|---|---|
| EP | 1310258 A1 | 5/2003 |
| WO | WO 97/06786 | 2/1997 |
| WO | WO 99/43329 A1 | 9/1999 |
| WO | WO 01/55692 A3 | 8/2001 |
| WO | WO 02/36128 C2 | 5/2002 |
| WO | WO 02/056892 A3 | 7/2002 |
| WO | WO 03/039555 A3 | 5/2003 |
| WO | WO 03/051348 A3 | 6/2003 |

OTHER PUBLICATIONS

Wolkowitz et al. Dehydroepiandrosterone (DHEA) treatment of depression. Society of Biological Psychiatry, 1997; 41, pp. 311-318.*
Stryjer et al. Amantadien as augmentation therapy in the management of treatment-resistant depression. International Clinical Psychopharmacology, Mar. 2003, vol. 18. No. 2, p. 93-96, abstract.*
Belanger et al. Dehydroepiandrosterone and 17b-estradiol improve locomotor activity in MPTP Monkeys. Society for Neuroscience Abstract Viewer and Itinerary Planner, 2003, vol. 2003, abstract No. 610.10.*
M. Cyr et al., (2000), *Drugs with Estrogen-like Potency and Brain Activity : Potential Therapeutic Application for the CNS*, Curr. Pharm. Des. 6, 1287-312.
M. Kawata, (1995), *Roles of Steroid hormones and their receptors in structural organization in the nervous system*, Neurosci. Res. 24, 1-46; B.S. McEwen and S.E. Alves, (1999), *Endocr. Rev.* 20, 279-307.
B.B. Sherwin, (1997), *Estrogen Effects on cognition in menopausal woman*, Neurology 48, S21-6.
J.W. Simpkins et al., (1994), *The Potential Role for Estrogen Replacement Therapy in the Treatment of the Cognitive Decline and Neurodegeneration Associated With Alzhimer's Disease*, Neurobiol. Aging 15.
M. Baldereschi et al., (2000), *Parkinson's disease and pakinsonlsm in a longitudinal study*, Neurology 55, 1358-63.
G. F. Wooten et al., *Are men at greater risk for Parkinson's disease than women?*, J Neurol Neurosurg Psychiatry 2004; 75: 637-639.
K.E. Lyons et al., *Gender Differences in Parkinson's Disease*, (1998). Clin. Neuropharmacol. 21, 118-21.
T. Di Paolo, *Modulation of Brain Dopamine Transmission by Sex Steroids*, (1994). Rev. Neurosci. 5, 27-41.
I.H. Zwain and S.S.C. Yen, *Dehydroepladrosterone: Biosynthesis and Metabolism in the Brain*, (1999). Endocrinology 140, 880-887.
T. Azuma et al., *Neurosteroids in cerebrospinal fluid in neurologic disorders*, (1993). J. Neurol. Sci. 120, 87-92.
M. D'Astous et al., (2003). *Ehydroepiandrosterone (DHEA) Such as 17β-Estradiol Prevents MPTP- Induced Dopamie Depletion in Mice*, Synapse 47, 10-14.
M.D. Majewska et al., *The neurosteroid dehydroepiandrosterone sulfate is an allosteric antagonist of the $GABA_A$ receptor* (1990). Brain Res. 526, 143-146.

(Continued)

*Primary Examiner*—Jennifer Myong M Kim
(74) *Attorney, Agent, or Firm*—Ogilvy Renault, LLP (57) ABSTRACT

The present invention concerns a method and a pharmaceutical composition for treating the symptoms associated to Parkinson's disease. The method and the pharmaceutical composition use a combination of a therapeutically effective amount of at least one of DHEA or DHEA-S in combination with a therapeutically effective amount of a dopamine precursor, such as levodopa. The present invention also concerns to the use of at least one of DHEA or DHEA-S in combination with a therapeutically effective amount of a dopamine precursor to manufacture a medicament for treating a neurodegenerative diseases.

9 Claims, 5 Drawing Sheets

OTHER PUBLICATIONS

S. Callier et al., 2000, *Stereospecific Prevention by 17β-Estradiol of MPTP-Induced Dopamine Depletion in Mice*, Synapse 37, 245-251.

M. Cyr et al., *Estrogenic modulation of brain activity: implications for schizophrenia and Parkinson's disease*, J. Psychiatry Neurosci 2002, 27(1):12-27.

S. Callier et al., *Neuroprotective Properties of 17β-Estradiol, Progestserone, and Raloxifene in MPTP C57Bl/6 Mice*, Synapse 41:131-138 (2001).

D. E. Dluzen et al., *Estrogen Alters MPTP-Induced Neurotoxicity in Female Mice : Effects on Striatal Dopamine Concentrations and Release*, J. Neurochem., vol. 66, No. 2, 1996, 658-666.

P. J. Blanchet et al., *Short-term effects of high-dose 17[beta]-estradiol in postmenopausal PD patients: A crossover study*, Neurology, vol. 53(1), Jul. 13, 1999, 91-95.

B. Gomez-Mancilla et al., Effect of estrogen and progesterone on L-Dopa induced dyskinesia in MPTP-treated monkeys, Neurosci Letters, 135(1992)129-132

P.J. Blanchet et al., Regulation of Dopamine Receptors and Motor Behavior Following Pulsatile and Continuous Dopaminergic Replacement Strategies in the MPTP Primate Model, ADV Neurol. 2001; 86:337-344.

D.C. Montgomery, 1991, Third Edition, Design and Analysis of Experiments, Ed. Whisley and Sons, p. 216.

B.S. McEwen and S.E. Ales, *Estrogen Actions in the Central Nervous System*(1999) Endocr Rev. 20, 279-307.

Morissette M. et al., 2008, "Contribution of estrogen receptors alpha and beta to the effects of estradiol in the brain.", Journal of Steroid Biochemistry & Molecular Biology, 108: 327-338.

\* cited by examiner

FIG. 1

LEGEND:
  ** P< 0.01 vs Vehicle
  ++ P<0.01 vs L-Dopa
  +  P< 0.05 vs L-Dopa
  †† P< 0.01 vs respective DHEA alone dose

COMBINED THERAPY FOR THE TREATMENT OF PARKINSON'S DISEASE

BACKGROUND OF THE INVENTION (a) Field of the Invention

The present invention relates to a method and a pharmaceutical composition for treating the symptoms associated to a neurodegenerative disease such as Parkinson's disease. The method and the pharmaceutical composition use a combination of a therapeutically effective amount of at least one of DHEA or DHEA-S in combination with a therapeutically effective amount of a dopamine precursor. The present invention also related to the use of at least one of DHEA or DHEA-S in combination with a therapeutically effective amount of a dopamine precursor for treating a neurodegenerative disease or to manufacture a medicament.

(b) Description of Prior Art

Parkinson's disease is attributable to a loss of dopamine in the brain caused by dopamine-producing nerve cells of the substantia nigra that begin to decrease in number and to the chemical break down of the remaining dopamine in the synapses. The deficient level of dopamine in Parkinson's patients throws off the normal dopamine/acetylcholine balance, since the level of acetylcholine remains normal. The dopamine/acetylcholine imbalance results in a lack of coordination of movements, tremors, stiff muscles and joints, and/or difficulty moving.

Unfortunately, no cure for Parkinson's disease is known thus far despite many attempts to stop the loss of dopamine-producing nerve cells or to restore those lost in the course of the disease. The only effective treatments available to Parkinson's patients are palliative therapies, which consist in helping patients to manage their slow decline by replacing or simulating the effect of the dopamine to compensate for the dopamine deficiency, slow down or reduce the ongoing loss of dopamine, or balance the level of acetylcholine with the level of dopamine in the brain.

Among the existing therapies for Parkinson's disease symptoms, levodopa, (L-3,4-dihydroxyphenylalanine) is one of the most effective medication for controlling the stiffness, tremors, spasms, and poor muscle control of Parkinson's disease patients. Levodopa is a dopamine precursor which is transported to the brain, picked up by the nerve cells that produce dopamine, converted into dopamine and further used as a neurotransmitter. Use of levodopa for dopamine replacement therapy can however constitute an effective mean to control the symptoms of Parkinson's disease for a limited period. Indeed, as the loss of dopamine-producing nerve cells continues, symptoms continue to worsen and consequently, the dose of levodopa administered to patients has to be increased. Over time, continual increases in the levodopa dose may eventually lead to the development of side effects which in many cases are so important that it becomes impossible to increase the dose of levodopa any higher.

To avoid levodopa-associated peripheral side effects, prior art reports the combination of that dopamine precursor with different compounds. For example, addition of carbidopa to levodopa (Sinemet®) delays the conversion of levodopa into dopamine until it reaches the brain, contributes to reduce the amount of levodopa needs and therefore preventing or diminishing some of the side effects that often accompany levodopa therapy. Combination of levodopa to benserazide (Prolopa®) prevents the conversion of levodopa into dopamine in the body, with the exception of brain, and therefore prevents side effects such as nausea and palpitations. However, these combined drugs are less likely effective to prevent motor complications such as wearing-off, on-off and dyskinesia, which are major drawbacks associated to dopamine-replacement therapies. In addition, these drug combinations are ineffective to prevent levodopa response fluctuations and the shortening of the effect of levodopa through the years of treatment.

One of the avenue envisioned in the recent years for the treatment of in neurodegenerative diseases such as Alzheimer and Parkinson (M. Cyr et al., (2000), *Curr. Pharm. Des.* 6, 1287-312) relates to the use of sex steroids. Indeed, estrogens and androgens (sex steroids) exert profound effects on brain differentiation, neural plasticity and central neurotransmission during development (M. Kawata, (1995), *Neurosci. Res.* 24, 1-46; B. S. McEwen and S. E. Alves, (1999), *Endocr. Rev.* 20, 279-307). In adult men and women, accumulating evidence supports a modulatory role of these steroids in the brain (B. B. Sherwin, (1997), *Neurology* 48, S21-6) and their prime importance in the normal maintenance of brain function during aging (J. W. Simpkins et al., (1994), *Neurobiol. Aging* 15, S195-7).

The role of sex steroids in Parkinson's disease is also illustrated by a greater prevalence and incidence of Parkinson's disease in men than in women (M. Baldereschi et al., (2000). *Neurology* 55, 1358-63; G. F. Wooten et al., (2004) *J. Neurol. Neurosurg. Psychiatry* 75, 637-639). Gender differences on evolution of symptoms and responses to levodopa treatment are also reported (K. E. Lyons et al., (1998). *Clin. Neuropharmacol.* 21, 118-21). Modulation of dopaminergic action pathway by estrogens is now well established. Symptoms of Parkinson's disease and levodopa-induced dyskinesias were also shown to be modulated by estrogens (T. Di Paolo, (1994). *Rev. Neurosci.* 5, 27-41).

Dehydroepiandrosterone (DHEA) and its sulfate derivative (DHEA-S) are sex steroid precursors of both estradiol and testosterone. These steroid precursors are also considered as being neurosteroids, since they have been shown to be synthesized in the brain (I. H. Zwain and S. S. C. Yen, (1999). *Endocrinology* 140, 880-887). Studies undergone to determine a role of DHEA and DHEA-S in Parkinson's disease suggested few time ago no particular function of these sex steroid precursors in Parkinson's disease, since no significant difference in cerebrospinal fluid DHEA and DHEA-S were found between Parkinson's disease patients and age-matched controls (T. Azuma et al., (1993). *J. Neurol. Sci.* 120, 87-92).

More recent evidences however report a role pf DHEA in Parkinson's disease. For example, international patent application published under number WO 01/55692 disclose methods and kits whereby the onset of neuropathology, such as Parkinson's disease, is detected by changes in the normal levels of neurosteroids, and particularly DHEA and its metabolic precursors, in the brain and serum. Modulation of dopaminergic activity by DHEA was also shown, but to a lower extent than estrogens. Moreover, DHEA was shown to have a protective role, protecting animals against a dopamine depletion caused by 1-methyl-4-phenyl-1,2,3,6-tetrahydropyridine (MPTP) (M. D'Astous et al., (2003). *Synapse* 47, 10-14).

Published U.S. patent application 2002/0182196 discloses a nutritional supplement composition for normalizing impaired or deteriorating neurological function in humans, such as those occurring in Parkinson's disease. This composition comprises at least one agent for normalizing or maintaining normal neurotransmitter function in the body, at least one agent for down-regulating cortisol action and several others components. Particularly, this composition may comprise DHEA for which action is limited to cortisol action modulation.

International patent application published under number WO 99/43329 discloses a composition for treatment of a human body comprises a combination of at least one hormone, at least one amino acid, at least one enzyme and/or vitamin, and at least one mineral. The hormone of the composition comprises DHEA and can be used in the treatment of the symptoms associated to Parkinson's disease.

Although DHEA and DHEA-S now seem to play a role in Parkinson's disease, many important side effects are associated to the administration of high doses of DHEA or DHEA-S. For example, acne, increased scalp itching, menstrual irregularities, irritability, restlessness, heart palpitations and scalp hair loss are associated with a DHEA increase in the body. Therefore, it is unlikely that Parkinson's disease therapies relying only on DHEA administration would be successful. Therefore, it would be highly desirable to be provided with a method that conjugates the effect of both DHEA and levodopa.

SUMMARY OF THE INVENTION

The present invention relates to a method for treating the symptoms associated to a neurodegenerative disease in a patient. The method of the present invention comprises concomitantly administering to the patient a therapeutically effective amount of at least one of dehydroepiandrosterone and dehydroepiandrosterone-sulfate with a therapeutically effective amount of a dopamine precursor.

The present invention also relates to a pharmaceutical composition for treating of the symptoms associated to a neurodegenerative disease and to a composition for use in the treatment of symptoms associated to a neurodegenerative disease. Compositions comprise a therapeutically effective amount of at least one of dehydroepiandrosterone and dehydroepiandrosterone-sulfate with a therapeutically effective amount of a dopamine precursor.

The present invention further relates to the use of a composition in the manufacture of a medicament for the treatment of symptoms associated to a neurodegenerative disease, where the composition comprises a therapeutically effective amount of at least one of dehydroepiandrosterone and dehydroepiandrosterone-sulfate with a therapeutically effective amount of a dopamine precursor.

The present invention finally relates to the use of a composition for the treatment of symptoms associated to a neurodegenerative disease, where the composition comprises a therapeutically effective amount of at least one of dehydroepiandrosterone and dehydroepiandrosterone-sulfate with a therapeutically effective amount of a dopamine precursor.

For the purpose of the present invention the following terms are defined below.

The term "MPTP" is intended to mean 1-methyl-4-phenyl-1,2,3,6-tetrahydropyridine.

The term "levodopa" is intended to mean L-(−)-2-amino-3-(3,4-dyhydrophenyl)propionic acid, L-3,4-dihydrophenylalanine, 3,4-dihydroxyphenyl-L-alanine, (−)-3-(3,4-dihydroxyphenyl)-L-alanine or 3-hydroxy-L-thyrosine.

DESCRIPTION OF THE PREFERRED EMBODIMENTS

The present invention provides a method for treating the symptoms associated to a neurodegenerative disease. The neurodegenerative disease of the present invention is any of disease, disorder, condition, sickness or illness that causes any degeneration, lesion, damage, deterioration or collapsing of neurons, preferably neurons of the substantia nigra and more preferably dopamine-producing neurons of the substantia nigra. The neurodegenerative disease includes any of Alzheimer's Disease (AD), Lewy body variant Alzheimer's Disease, amyotrophic lateral sclerosis, dementia, multiple system atrophy, neuronal intranuclear inclusion disease, Parkinson's disease, prion related diseases, tauopathies, trinucleotide repeat diseases and Tourettes syndrome. The disease is however preferably Parkinson's disease.

By treating the symptoms of the neurodegenerative disease, it is intended to mean any way for alleviating, relieving, curing, healing, reducing or improving the symptoms associated to the neurodegenerative disease, and should not be restricted to total or complete disappearance of the symptoms. For the purpose of the present invention, symptoms are those generally associated to neurodegenerative diseases and include tremors, muscle stiffness, joint stiffness, spasm, low muscle control, movement difficulty, ipsilateral circling, rigidity in arms, rigidity in legs, reduced locomotor activity, movement coordination or a combination of these symptoms. For example, the method and the pharmaceutical composition of the present invention showed that DHEA significantly improves the levodopa-induced locomotor activity and contralateral circling. DHEA improvement of levodopa-induced treatments of neurodegenerative diseases' symptoms may occur by any DHEA action pathway known in the prior art. For example, levodopa-induced locomotor activity or contralateral circling in MPTP-monkeys may occur through the binding of DHEA to an allosteric site on GABAa receptors, DHEA-S being known in the art to behave as a negative modulator of the GABAa receptor complex (M. D. Majewska et al., (1990). *Brain Res.* 526, 143-146.). DHEA being a precursor of 17β-estradiol, DHEA and DHEA-S may potentiate levodopa-induced activity by acting as an estrogenous pro-drug, since enzymes responsible for the transformation of DHEA into 17β-estradiol are expressed in the brain (I. H. Zwain and S. S. C. Yen, (1999). *Endocrinology* 140, 880-887).

The dopamine precursor of the present invention is administered concomitantly to DHEA or DHEA-S. By concomitant administration, it is intended any form of administration that enables the potentiation of dopamine precursor-induced treatment of the symptoms associated to a neurodegenerative condition. Such concomitant administration include any form of administration in which DHEA, DHEA-S and/or dopamine precursors are administered together, such as in association in a pharmaceutical composition, or separately. A separate administration of DHEA, DHEA-S and dopamine precursor is preferably performed within a time frame that enables each of these compounds or a combination of these compounds to enter into blood circulation, go by the hematoencephalic barrier and exert its action into the brain, where the action of one compound potentiates the action of another one. The concomitant administration of least one of dehydroepiandrosterone and dehydroepiandrosterone-sulfate with a therapeutically effective amount of a dopamine precursor may be performed by any administration route known in the prior art and includes, but is not limited to rectal, buccal, sublingual, intravenous, subcutaneous, intradermal, transdermal, intraperitoneal, oral, parenteral and topical administration.

Oral administration includes gavage, nasogastric gavage and any administration mode that makes use of a solid or liquid pharmaceutical composition comprising at least one of DHEA, DHEA-S and dopamine precursor and suitable for oral administration. The pharmaceutical composition suitable for oral administration may be presented as discrete units such as capsules, cachets, caplets or tablets, each containing a predetermined amount of at least one of DHEA, DHEA-S and dopamine precursor, as a powder or granules or as a solution or suspension in an aqueous liquid, a non-aqueous liquid, an oil-in-water emulsion or a water-in-oil emulsion. Such compositions may be prepared by any of the methods of pharmacy, including the step of bringing the DHEA, DHEA-S, dopamine precursor or combination thereof into association with the carrier which includes one or more necessary ingredients. In general, the compositions are prepared by uniformly and intimately admixing the DHEA, DHEA-S or dopamine precursor with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Moulded tablets may be made by moulding, in a suitable machine, a mixture of the DHEA, DHEA-S or dopamine precursor moistened with an inert liquid diluent.

The mode of administration by injection includes continuous infusion as well as single or multiple boluses. Useful administration types or modes also include the use of pumps, such as implantable internal pumps, for continuous infusion into a blood vessel or at different sites such as the peritoneal cavity or subcutaneously, as disclosed in the art. The DHEA, DHEA-S, dopamine precursor or combination thereof can be formulated as a sterile pharmaceutical composition for therapeutic use which is suitable for intravenous or intraarterial administration. The product may be in a solvent-free form and ready to be reconstituted for use by the addition of a suitable carrier or diluent, or alternatively, it may be in the form of an aqueous or organic solution. For reconstitution of a solvent-free product in accordance with the present invention, one may employ a sterile diluent, which may contain materials generally recognized for approximating physiological conditions. In this manner, the sterile diluent may contain salts and/or buffering agents to achieve a physiologically acceptable tonicity and pH, such as sodium chloride, phosphate and/or other substances which are physiologically acceptable and/or safe for use.

When used as an aqueous solution, the pharmaceutical composition will for the most part contain many of the same substances described above for the reconstitution of solvent-free product. When used in solution in an organic solvent, a small volume of the solution containing the DHEA, DHEA-S, dopamine precursor or combination thereof will be diluted with an aqueous solution that will contain many of the same substances described above for the reconstitution of a solvent-free product. The pharmaceutical composition, for the most part, will thus contain many of the same substances described above for the reconstitution of a solvent-free product. Pharmaceutical composition, method and uses that are the object of the present invention may make use of sterile solutions for injection, encapsulated in liposomes or embedded, for example in suppositories, for slower long-lasting release. Suitable vehicles and their formulations, including human proteins, such as human serum albumin, are described for instance in the background art.

Transdermal administration includes administration by means of a patch, cream, ointment, balm, unguent, emulsion, lotion or lotion that comprises at least one of DHEA, DHEA-S and dopamine precursor.

The dopamine precursor used for the purpose of the present invention is preferably levodopa, also commonly known as, L-3,4dihydrophenylalanine, L-dopa or T.L-dopa or any derivative thereof. Such levodopa derivative includes levodopa methyl ester (LDME) (U.S. Pat. No. 4,826,875) or L-meta-tyrosine (U.S. Pat. No. 3,838,008), levodopa ethyl ester (LDEE)(U.S. Pat. No. 6,696,600) or salt thereof. Levodopa derivative salt includes, but is not limited to fumarate salt, fumarate dihydrate salt, hydrochloride salt, the hydrobromide salt, the nitrate salt, perchlorate salt, phosphate salt, sulfate salt, formate salt, acetate salt, aconite salt, ascorbate salt, benzosulphonate salt, benzoate salt, cinnamate salt, citrate salt, embonate salt, enantate salt, fumarate salt, glutamate salt, glycolate salt, lactate salt, maleate salt, malonate salt, mandelate salt, methane sulphonate salt, myristate salt, octanoate salt, phthalate salt, salicylate salt, sorbate salt, stearate salt, succinate salt, succinate dihydrate salt, tartrate salt and the like. Such salts may be obtained following procedures known in the art.

Dopamine precursor, alone or in combination with DHEA, DHEA-S or a combination thereof, can be administered concurrently to at least one of a carrier and a therapeutic agent. Therapeutic agent includes, but is not limited to, exogenous dopamine, agents that will be metabolized into the organism so as to provide dopamine to the brain, such as dopamine precursors, dopamine agonist, therapeutic agents that enhance the release of dopamine stored by the dopamine-producing neurons, therapeutic agents that contribute to adjust acetylcholine level to provide a suitable dopamine/acetylcholine balance, catechol-O-methyl transferases (COMT), monoamine oxidase B inhibitors, monoamine reuptake inhibitors, Dopamine decarboxylase inhibitors, dopamine activity enhancers or a combination thereof. Examples of such agents known in the art include bromocriptine, bromocriptine mesylate (Parlodel®), pergolide, pergolide mesylate (Permax®), amantadine hydrochloride (Symmetrel®), trihexyphenidyl HCl (Artane®), benztropine mesylate (Cogentin®), pramipexole (Mirapex®), ropinirole hydrochloride (Requip®), tolcapone, cabergoline, apomorphine, domperidone, entacapone selegiline, carbidopa (Sinement®), benserazide (Prolopa®), (Bupropion®), Nomifensine® or the like.

The carrier to which is combined DHEA or DHEA-S and dopamine precursor or a combination thereof is a pharmaceutically acceptable carrier. In practical use, these compounds can be combined as active ingredients in intimate admixture with a pharmaceutical carrier according to conventional pharmaceutical compounding techniques. The carrier may take a wide variety of forms depending on the form desired for administration. In preparing the compositions for oral dosage form, any of the usual pharmaceutical media may be employed, such as, water, glycols, oils, alcohols, flavouring agents, preservatives, coloring agents and the like in the case of oral liquid preparations (for example, suspensions, elixirs, and solutions), or carriers such as starches, sugars, microcrystalline celluloses, diluents, granulating agents, lubricants, binders, disintegrating agents and the like in the case of oral solid preparations (for example, powders, capsules, and tablets). If desired, tablets may be coated by standard aqueous or non aqueous techniques.

In addition to the herein-above described carrier, additional pharmaceutical methods may be employed to control the duration of the action of DHEA or DHEA-S and dopamine precursor or combination thereof. For example, controlled-release preparations may be achieved through the use of macromolecules forming complexes with or absorbing the DHEA or DHEA-S and dopamine precursor or combination thereof. The controlled delivery may be achieved by selecting appropriate macromolecules, for example, polyesters, polyamino acids, polyvinyl pyrrolidone, ethylene-vinyl acetate, methyl cellulose, carboxymethyl cellulose, protamine sulfate or serum albumin, the appropriate concentration of macromolecules, as well as the methods of incorporations. In this manner, release of DHEA or DHEA-S and dopamine precursor or combination thereof can be controlled. Another possible method useful in controlling the duration of action by controlled release preparations is the incorporation of DHEA or DHEA-S and dopamine precursor or combination thereof into particles of a polymeric material such as polyesters, polyamino acids, hydrogels, poly(lactic acid), or ethylene-vinyl acetate copolymers. Instead of incorporating the DHEA or DHEA-S and dopamine precursor or combination thereof into polymeric particles, it is also possible to entrap it in microcapsules prepared, for instance, by coacervation techniques or by interfacial polymerization (for example hydroxymethyl cellulose or gelatine microcapsules and polymethyl methacrylate microcapsules, respectively), in colloidal drug delivery systems (for example, liposomes, albumin microspheres, microemulsion, nanoparticles and nanocapsules) or in macroemulsions. Such techniques are well known in the art.

The patient of the present invention is an animal, and preferably a mammal, and more preferably a murine, a feline, a canine, a monkey or a human. However, any animal that may benefit from the concomitant administration of a therapeutically effective amount of at least one of dehydroepiandrosterone and dehydroepiandrosterone-sulfate with a therapeutically effective amount of a dopamine precursor is part of the invention.

The present invention will be more readily understood by referring to the following examples which are given to illustrate the invention rather than to limit its scope.

EXAMPLE 1

Potentialisation of Levodopa Activity by Dhea Administration to Mptp-Monkeys

Materials and Methods

Six hemiparkinsonian ovariectomized female *macaca fasicularis* monkeys weighing 2.8-6.5 kg were used in this experiment. During induction of the parkinsonian syndrome, they received 1-methyl-4-phenyl-1,2,3,6-tetrahydropyridine (MPTP, 3 mg) via an Alzet pump during a period of 1-2 weeks according to the monkey. The procedure consisted of putting the pump in the left substantia nigra and the MPTP infused lesioned the dopaminergic cells. The animals were used at least 5 months after the induction of their hemiparkinsonian state at which time they had stabilized. For a further experimentation, 6 bilaterally-lesioned parkinsonian *macaca fasicularis* monkeys were used. The induction of the parkinsonian syndrome was performed according to the above-described methodology, except that the Alzet pump was installed so as to lesion dopaminergic cells of the substantia nigra in both brain hemispheres.

To determine the effect of levodopa, DHEA or combination thereof on parkinsonian monkeys, ipsilateral and contralateral circling was monitored in hemiparkinsonian monkeys while Parkinsonian score was determined in bilaterally-lesion parkinsonian monkeys. Hemiparkinsonian monkeys turn towards the ipsilateral side of the lesion (to the left) under basal conditions and upon dopaminergic stimulation this circling changes for the contralateral side (to the right). Parkinsonian score was determined in bilaterally-lesion parkinsonian monkeys according to the method known in the art. All received the same treatments and were their own controls. Monkeys were first treated with levodopa for priming until a stable antiparkinsonian behavior was observed. During the investigation of DHEA administered alone, priming of the monkeys was continued with administration of levodopa/benserazide (50/12.5 mg) given twice weekly. DHEA treatments were started on the third day after the last levodopa dose. When treatments involved a combination of levodopa with DHEA, the monkeys did not receive additional levodopa priming.

DHEA was administered at different doses (1, 5, and 15 mg/kg) by nasogastric gavage (n.g.) alone and in combination (DHEA: 1, 5, 10 and 15 mg/kg n.g.) with a s.c. T.L-Dopa. Threshold doses of levodopa, that is the minimal dose to obtain contralateral circling were sought for each of the MPTP-monkeys and varied from one monkey to another from 3 to 8 mg/kg (3, 4, 4.5, 5, 5, and 8 mg/kg). Higher doses of DHEA (25-100 mg/kg) alone or with T.L-Dopa were also tested in a similar paradigm.

Treatments were administered in the morning and each animal was recorded via a video camera system. Duration of locomotor activation lasted for 90 min for all hemiparkinsonian animals and treatments. Hence, behavior was measured for 90 min with left and right circling quantified for 30-minute periods. Each treatment was repeated 2-3 times and averaged for each monkey. Saline and T.L-Dopa treatments were performed in the beginning and the end of each different hormonal treatment and found not significantly different. Hence, these values were grouped.

Experimental data was compared using an ANOVA for repeated measures followed by post-hoc pair wise comparisons with Fisher's probability of least significant difference test (PLSD). A $p<0.05$ was required for the results to be considered statistically significant. Statistical comparison of square root transformation of the data was used to stabilize variance when required (D. C. Montgomery (1991) Third Edition, *Design and analysis of experiments*. ed. Whileys and Sons pp. 216).

Results

The hemiparkinsonian and bilaterally-lesion parkinsonian MPTP-monkeys under basal conditions or after saline treatment displayed ipsilateral circling behavior (hemiparkinsonian monkeys) or parkinsonian symptoms (bilaterally-lesion parkinsonian monkeys). After dopaminergic stimulation with DHEA alone, DHEA combined to T.L-Dopa, they decreased their ipsilateral circling and started turning to the contralateral side relative to the lesion or the parkinsonian symptoms were reduced.

Figure 1:
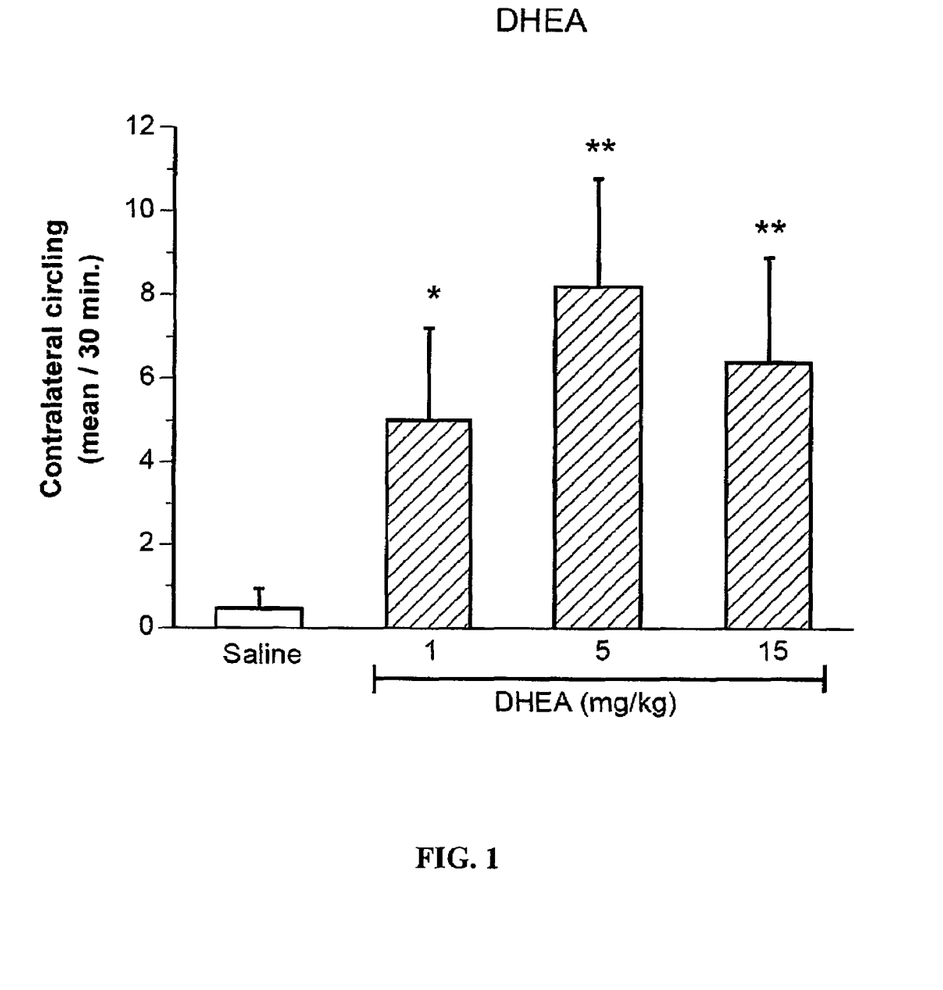
FIG. 1 illustrates the effect of DHEA on contralateral circling in hemiparkinsonian MPTP-monkeys behavior by comparison to saline.
Figure 2:
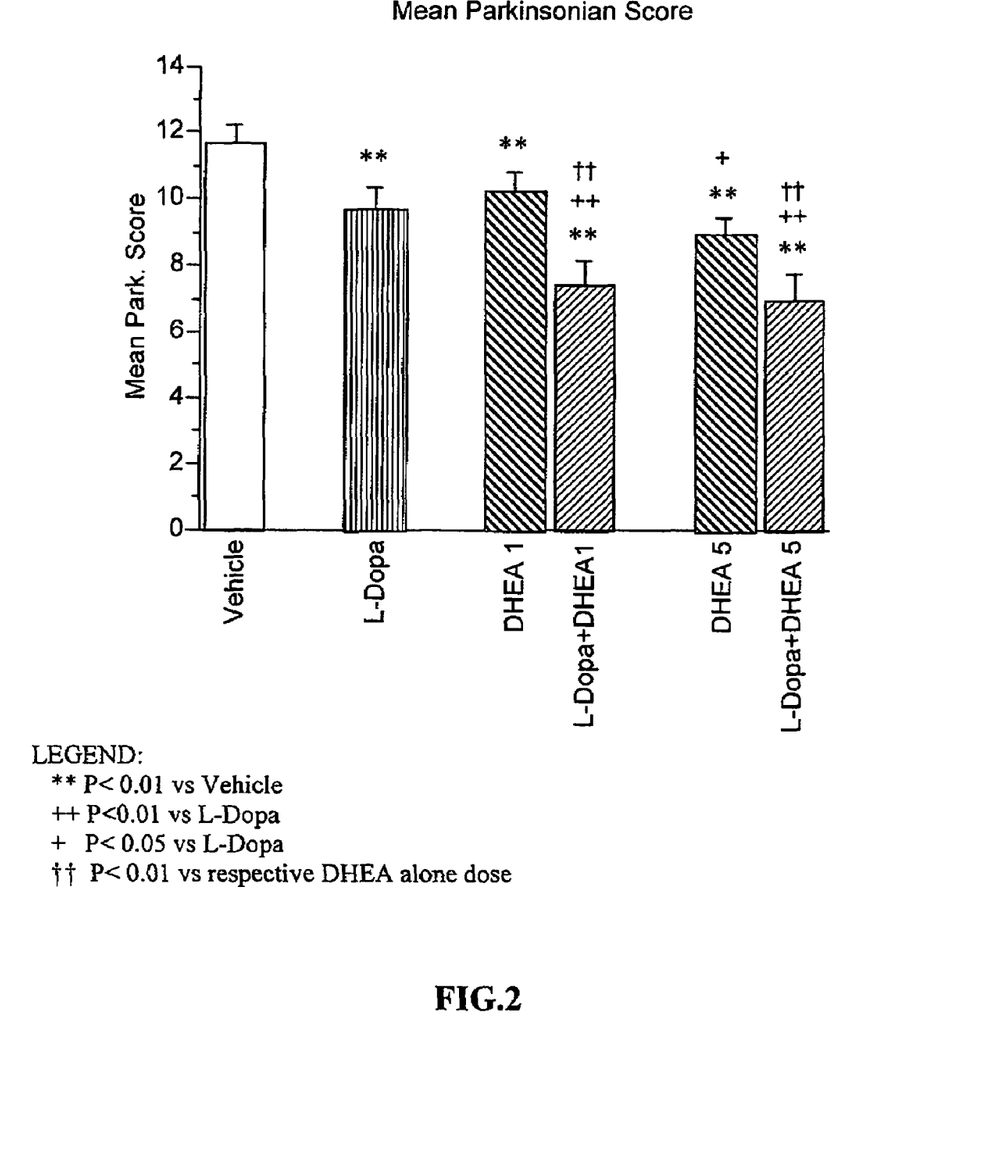
FIG. 2 illustrates the effect of DHEA, alone o in combination with a threshold dose of levodopa on Parkinsonian score in bilaterally-lesioned parkinsonian MPTP-monkeys, by comparison to levodopa alone or saline treatment.
Figure 3:
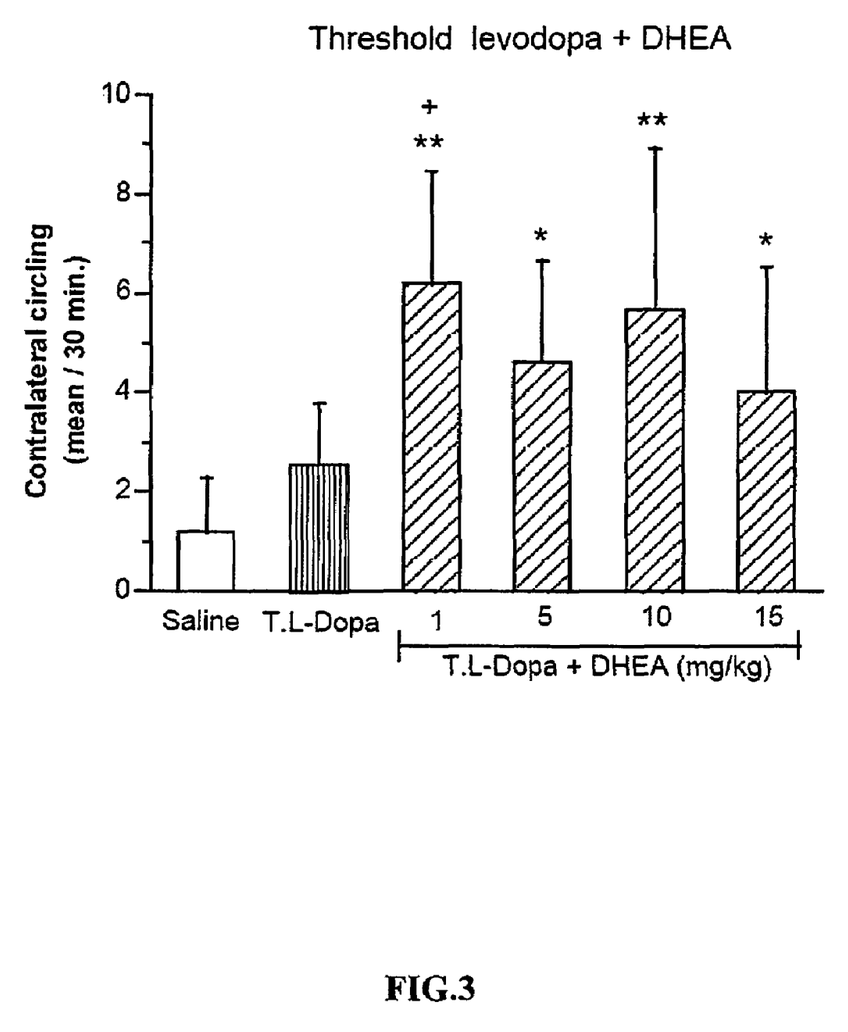
FIG. 3 illustrates the effect of DHEA in combination with a threshold dose of levodopa on contralateral circling behavior in hemiparkinsonian MPTP-monkeys, by comparison to levodopa alone or saline treatment.
Figure 4:
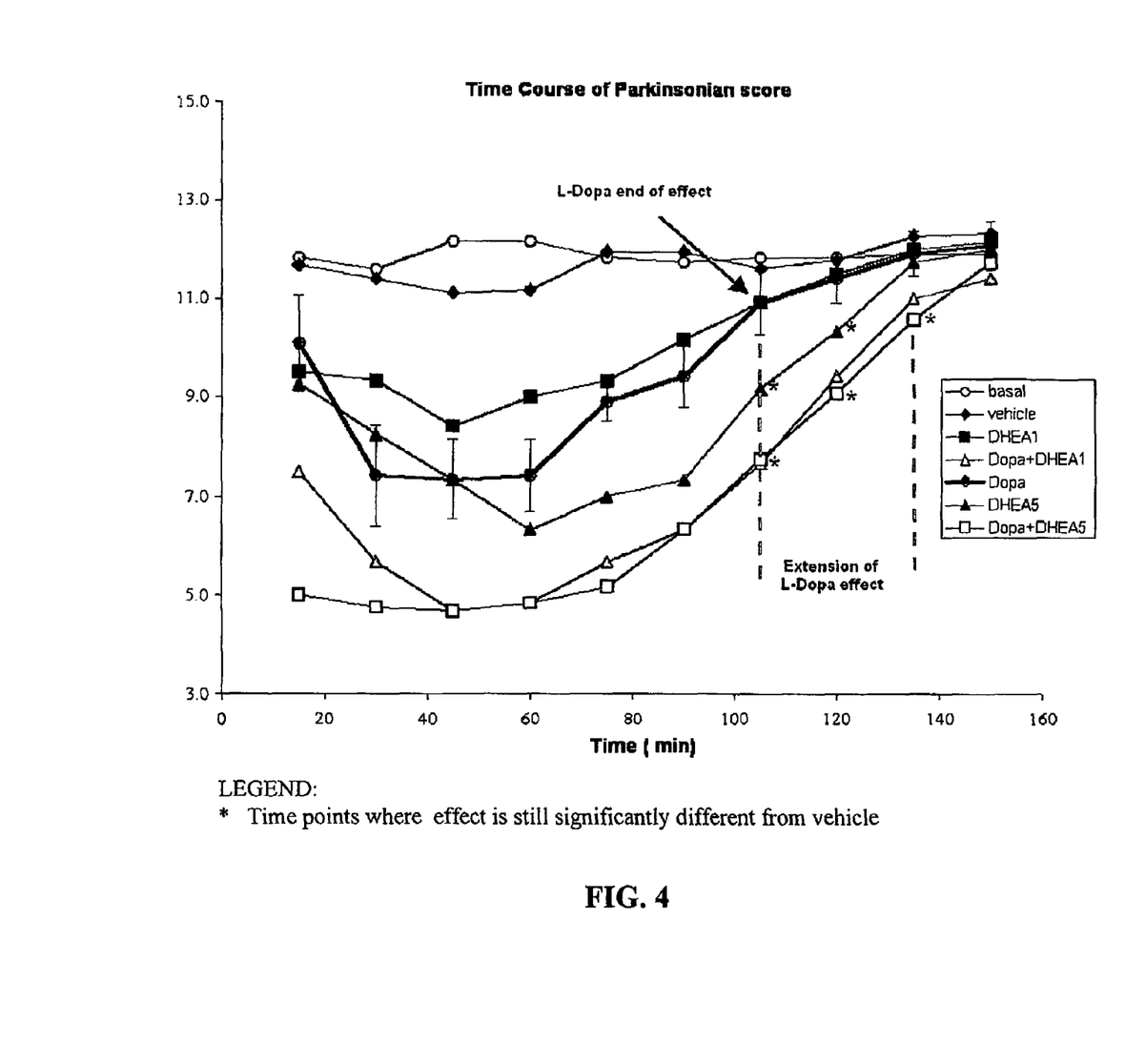
FIG. 4 illustrates the effect of DHEA, alone or in combination with a threshold dose of levodopa on the duration of the levodopa-induced effect in bilaterally-lesioned parkinsonian MPTP-monkeys, by comparison to levodopa alone or saline treatment.

DHEA alone investigated at different doses was able to induce contralateral circling and reduce the Parkinsonian score, as shown in FIG. 1 and FIG. 2. Thus, 1-15 mg/kg of DHEA significantly and similarly increased contralateral circling (mean/30 min) compared to saline treatment. Duration of the DHEA effect lasted for 90 min. The effect of DHEA at different doses with a T.L-Dopa is shown in FIG. 2 and FIG. 3. The smallest dose of dose of DHEA (1 mg/kg) added to T.L-Dopa significantly increased contralateral circling (mean/30 min) and decreased the Parkinsonian score compared to saline or T.L-Dopa treatment alone. T.L-Dopa combined with higher doses of DHEA (5, 10 and 15 mg/kg) significantly increased the contralateral circling (mean/30 min) and reduced the Parkinsonian score compared to saline treatment. Higher doses of DHEA (25-100 mg/kg) alone or in combination with T.L-Dopa gave similar results. DHEA treatment (1 and 5 mg/kg) also changed the duration of levodopa effect, which was increased from approximately 40% at both DHEA concentrations (FIG. 4).

Figure 5:
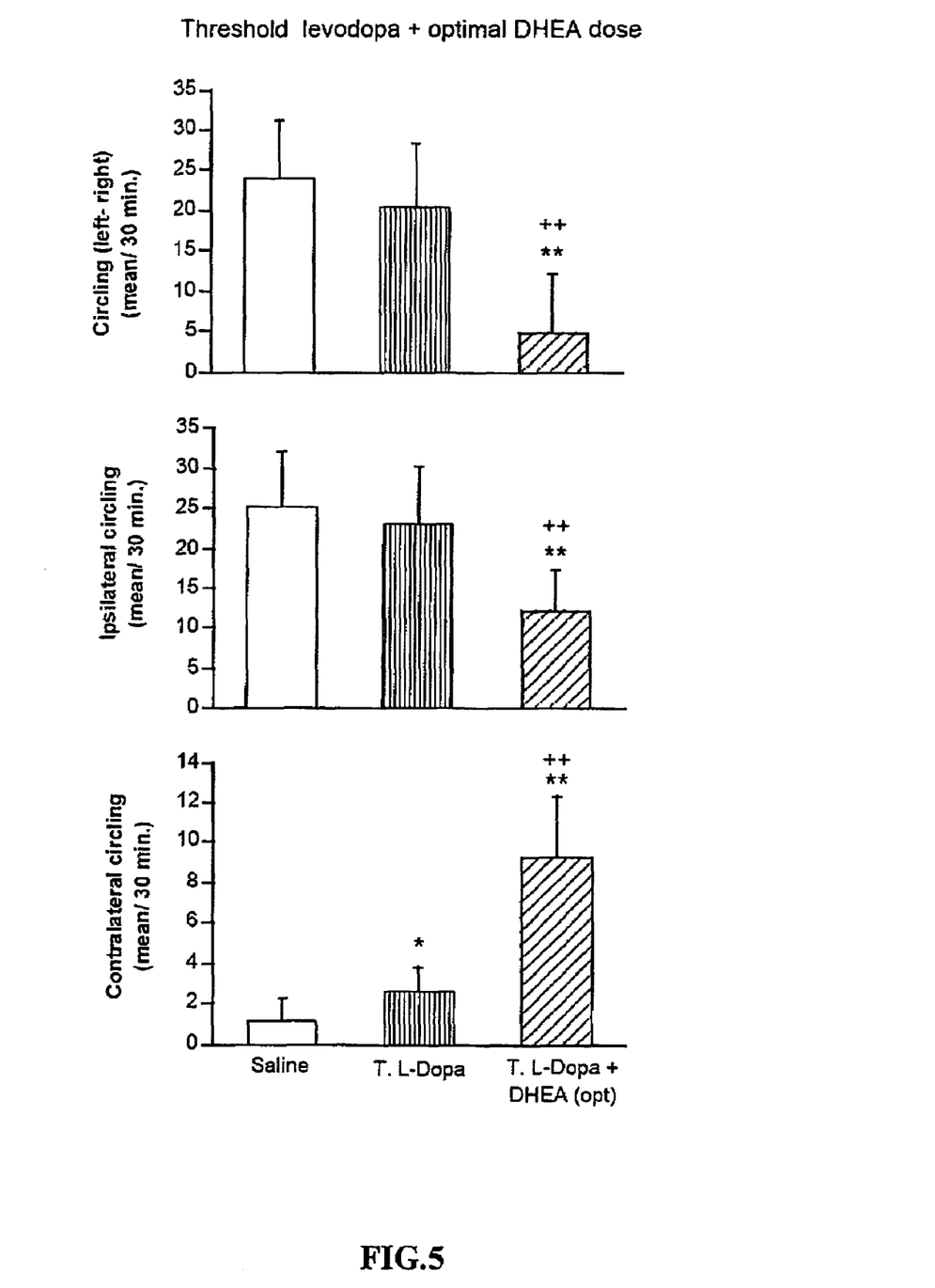
FIG. 5 illustrates the effect of optimal DHEA dose in combination with a threshold levodopa dose on ipsilateral and contralateral circling in hemiparkinsonian MPTP-monkeys, by comparison to levodopa alone or saline treatment.

DHEA alone or combined with levodopa did not produce a significant dose-response on circling behavior. A maximal response was obtained with different doses in the monkeys tested for DHEA alone or combined with levodopa. Hence, in FIG. 5 is shown the mean of the optimal dose of DHEA for each monkey for ipsilateral, contralateral and their difference (ipsilateral-contralateral). Levodopa increased contralateral and decreased ipsilateral circling thus reducing the overall ipsilateral-contralateral circling. The optimal dose of DHEA combined with DHEA significantly potentiated this effect. A maximal response was observed with 1 or 5 mg/kg of DHEA combined with levodopa depending on the monkey. No correlation was found between the dose for the maximal response and baseline circling or threshold dose of levodopa.

In conclusion, DHEA potentiates levodopa-induced locomotor activity in a MPTP-monkey model of Parkinson's disease. The effective doses of DHEA are in the range used safely in humans. The present paradigm used minimal threshold doses of levodopa. Hence, adding DHEA to levodopa therapy could enable the reduction of the dose of levodopa and hence protect against the side effects associated with this drugs, which are dose-related. Finally, DHEA contributes to prolong the effects of levodopa.

While the invention has been described in connection with specific embodiments thereof, it will be understood that it is capable of further modifications and this application is intended to cover any variations, uses, or adaptations of the invention, following, in general, the principles of the invention, and including, such departures from the present disclosure as come within known or customary practice within the art to which the invention pertains and as may be applied to the essential features hereinbefore set forth, and as follows in the scope of the appended claims.

I claim:

1. A method for treating at least one motor symptom associated to Parkinson's disease in a patient suffering therefrom which comprises concomitantly administering to said patient a therapeutically effective amount of at least one of dehydroepiandrosterone and dehydroepiandrosterone-sulfate with a therapeutically effective amount of a dopamine precursor.

2. The method of claim 1, wherein said dopamine precursor comprises levodopa or a derivative thereof.

3. The method of claim 2, wherein said levodopa or said derivative thereof is to be used concurrently with at least one of a carrier and a therapeutic agent.

4. The method of claim 3, wherein said therapeutic agent is selected from the group consisting of: bromocriptine mesylate, pergolide mesylate, amantadine hydrochloride, trihexyphenidyl HCl, and benztropine mesylate, or a pharmaceutically acceptable salt thereof.

5. The method of claim 1, wherein said said dehydroepiandrosterone, said dehydroepiandrosterone-sulfate and said dopamine precursor are administered separately.

6. The method of claim 1, wherein anyone of said dehydroepiandrosterone, said dehydroepiandrosterone-sulfate and said dopamine precursor is administered by anyone of the route consisting of: rectal, buccal, sublingual, intravenous, subcutaneous, intradermal, transdermal, intraperitoneal, oral, parenteral and topical administration.

7. The method of claim 1, wherein said patient is a mammal.

8. The method of claim 7, wherein said mammal is selected from the group consisting of human, simian, feline, canine and murine.

9. The method according to claim 1, wherein said motor symptom is selected from the group consisting of: tremors, muscle stiffness, joint stiffness, spasm, low muscle control, movement difficulty, ipsilateral circling, rigidity in arms, rigidity in legs, reduced locomotor activity, and movement coordination, or any combination thereof.

\* \* \* \* \*

UNITED STATES PATENT AND TRADEMARK OFFICE
CERTIFICATE OF CORRECTION

| | | |
|---|---|---|
| PATENT NO. | : 7,576,073 B2 | Page 1 of 1 |
| APPLICATION NO. | : 10/855493 | |
| DATED | : August 18, 2009 | |
| INVENTOR(S) | : Thérèse Di Paolo | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this

Seventh Day of September, 2010

David J. Kappos
*Director of the United States Patent and Trademark Office*